(12) United States Patent
Clemen, Jr.

(10) Patent No.: US 9,244,023 B2
(45) Date of Patent: Jan. 26, 2016

(54) SYSTEMS AND METHODS FOR RADIATION MONITORING

(71) Applicant: The Boeing Company, Seal Beach, CA (US)

(72) Inventor: Mark J. Clemen, Jr., Bremerton, WA (US)

(73) Assignee: The Boeing Company, Chicago, IL (US)

( * ) Notice: Subject to any disclaimer, the term of this patent is extended or adjusted under 35 U.S.C. 154(b) by 347 days.

(21) Appl. No.: 14/183,168

(22) Filed: Feb. 18, 2014

(65) Prior Publication Data

US 2015/0276627 A1 Oct. 1, 2015

(51) Int. Cl.
| | |
|---|---|
| *G01N 23/10* | (2006.01) |
| *G01N 23/12* | (2006.01) |
| *G01V 5/02* | (2006.01) |
| *G01V 5/00* | (2006.01) |
| *G01T 7/00* | (2006.01) |
| *B64G 1/40* | (2006.01) |
| *G01N 21/64* | (2006.01) |

(52) U.S. Cl.
CPC .............. *G01N 23/12* (2013.01); *G01V 5/0075* (2013.01); *G01V 5/025* (2013.01); *B64G 1/40* (2013.01); *B64G 1/401* (2013.01); *G01N 21/64* (2013.01); *G01T 7/00* (2013.01)

(58) Field of Classification Search
CPC ....... G01N 23/12; G01N 23/10; G01N 21/64; G01V 5/0075; G01V 5/02; G01V 5/00; G01V 5/025; G01T 1/20; G01T 1/204; G01T 17/00; B64G 1/40; B64G 1/401
See application file for complete search history.

(56) References Cited

U.S. PATENT DOCUMENTS

| | | | | | |
|---|---|---|---|---|---|
| 2,952,774 | A | * | 9/1960 | Howard ............... | B64D 37/005 378/52 |
| 5,173,607 | A | * | 12/1992 | Yrjonen ................... | G01T 7/00 250/328 |
| 5,723,338 | A | * | 3/1998 | Rutledge .............. | G01N 21/643 436/172 |
| 8,352,105 | B2 | * | 1/2013 | Barnes ...................... | G01T 7/00 701/21 |
| 2004/0226355 | A1 | * | 11/2004 | Cho ..................... | F02M 55/025 73/114.47 |
| 2013/0313370 | A1 | * | 11/2013 | Rakers .................. | G01F 23/288 244/172.2 |

OTHER PUBLICATIONS

Fernandez et al., "Gasolines as Primary Solvents in Liquid Scintillation Counting," Rev. Sci. Instrum., 57, 2877, (1986).
Chen, "Scintillation and Light Sensitive Detectors—I," Queen's University, presentation (2007). Downloaded from http://neutron.physics.ucsb.edu/docs/ on Feb. 14, 2014.

(Continued)

*Primary Examiner* — Yara B Green
(74) *Attorney, Agent, or Firm* — DASCENZO Intellectual Property Law, P.C.

(57) ABSTRACT

Systems and methods for radiation monitoring with a fuel-based liquid scintillant are disclosed. Fuel-scintillant compositions according to this disclosure may serve dual purposes of a fuel to power an engine and a scintillator to detect radiation. For example, fuel-scintillant compositions may be incorporated into a radiation monitoring vehicle that combusts the fuel-scintillant composition to power the vehicle. Further, systems may be configured to detect scintillation events within the fuel-scintillant composition and may be configured to detect weak and/or distance radiation sources.

20 Claims, 4 Drawing Sheets

(56) References Cited

OTHER PUBLICATIONS

"Neutron-Gamma Discrimination with Stilbene and Liquid Scintillators," PerkinElmer Instruments—ORTEC, (2001). Downloaded from http://www.ortec-online.com/download/Neutron-Gamma-Discrimination-Stilbene-Liquid-Scintillators.pdf on Jan. 17, 2014.

Wurm, "R&D on Liquid-Scintillation Detectors," R&D and Astroparticle Physics, Lisbon, presentation, (Jan. 8, 2008). Downloaded from http://indico.cern.ch/event/24480/material/slides/1?contribId=5 on Jan. 17, 2014.

Xiao, "Oxygen Quenching in LAB Based Liquid Scintillator and Nitrogen Bubbling Model," erXiv:0904.1329v4 [nucl-ex] (Jul. 3, 2009).

* cited by examiner

SYSTEMS AND METHODS FOR RADIATION MONITORING

FIELD

The present disclosure relates to systems and methods for radiation monitoring.

BACKGROUND

Radioactive materials and radiation sources can be detected with radiation detectors, commonly scintillation detectors. Scintillation detection requires a special material, a scintillator, that luminesces when excited by radiation. Scintillators may be used in solid or liquid form. Only particular compositions, generally aromatic hydrocarbons, are scintillators in liquid form.

Detection of weak radiation sources (e.g., infrequent radiation events) and/or distant radiation sources generally requires large scintillation detectors for effective detection. Large detectors may be expensive, difficult to build, and/or difficult to move. Additionally, liquid scintillators may include large fractions of undesirable materials.

Hence, there is a need for systems and methods for radiation monitoring that economically may detect weak and/or distant sources and/or do so with less exotic and/or undesirable materials.

SUMMARY

Systems and methods for radiation monitoring may include, and/or may use, fuel-scintillant compositions that operate as a scintillation material and as a fuel. Fuel-scintillant compositions include a scintillant solution that is a hydrocarbon fuel for an engine. The scintillant solution may substantially be a conventional fuel. The scintillant solution includes a hydrocarbon solvent and a scintillator, and may include a primary luminophore, a secondary luminophore, a neutron sensitive adjunct, and/or a scintillation enhancer.

Systems and methods for radiation monitoring may include, and/or may use, radiation detection systems, such as radiation detection vehicles. Radiation detection systems include a fuel tank configured to contain a fuel-scintillant composition and an engine configured to consume the fuel-scintillant composition. Radiation detection systems, and radiation detection vehicles, may be configured to detect weak and/or distant radiation sources.

Methods for radiation monitoring may include detecting scintillation emission light from a fuel-scintillant composition to detect radiation, consuming the fuel-scintillant composition, e.g., consuming with an engine. Methods may include selecting a fuel-scintillant composition and/or forming a fuel-scintillant composition. Methods also may include detecting weak and/or distant radiation sources, and determining properties of the radiation.

DESCRIPTION

FIGS. 1-5 illustrate scintillation materials 10, radiation detection systems 40, and components thereof. Elements that serve a similar, or at least substantially similar, purpose are labeled with numbers consistent among the figures. Like numbers in each of FIGS. 1-5, and the corresponding elements, may not be discussed in detail herein with reference to each of FIGS. 1-5. Similarly, all elements may not be labeled in each of FIGS. 1-5, but reference numerals associated therewith may be used for consistency. Elements, components, and/or features that are discussed with reference to one or more of FIGS. 1-5 may be included in and/or used with any of FIGS. 1-5 without departing from the scope of the present disclosure. In general, elements that are likely to be included are illustrated in solid lines, while elements that may be optional or alternatives are illustrated in dashed lines. However, elements that are shown in solid lines are not necessarily essential, and an element shown in solid lines may be omitted without departing from the scope of the present disclosure.

Figure 1:
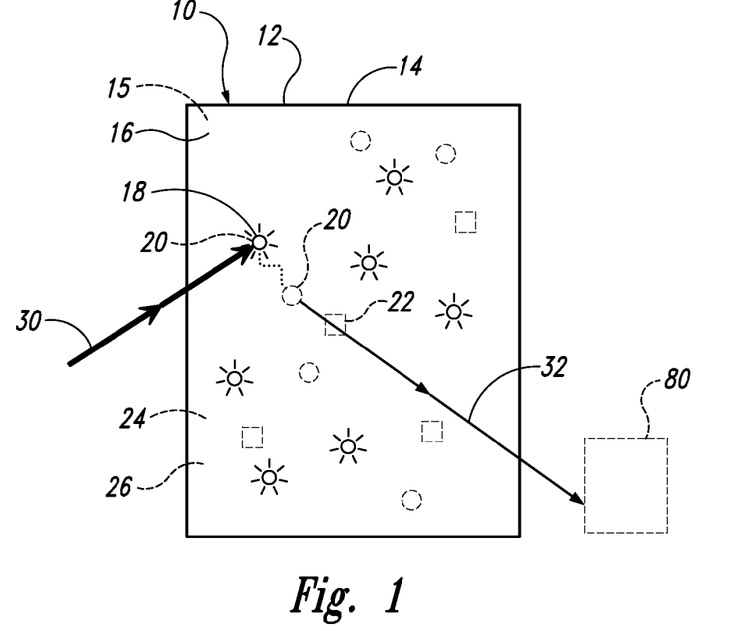
FIG. 1 is a schematic representation of scintillation materials.

FIG. 1 is a schematic representation of scintillation materials 10 with radiation 30 impinging thereupon. Radiation 30 (also referred to as ionizing radiation 30) is composed of subatomic particles (e.g., neutrons, protons, or nuclei) and/or high energy photons (e.g., gamma radiation, also known as gamma rays, x-rays, or extreme ultraviolet radiation) that have enough energy to ionize an atom or molecule. Radiation 30 is nearly ubiquitous in the natural environment, primarily from naturally-occurring radioactive materials and cosmic rays. Natural radiation sources include gamma ray bursts from space and terrestrial gamma ray flashes. Artificial radiation sources include radioisotopes and nuclear materials for energy production or weapons.

Radiation 30 is not directly perceptible but may be detected by a variety of phenomena. For example, certain materials (i.e., scintillation materials 10) emit light when exposed to radiation 30, in a process known as scintillation. The scintillation materials 10 include a luminophore, a molecule (or atom) that emits light (electromagnetic radiation) after being excited. Luminophores may be classified as fluorophores, with a fast excited state decay time (typically picoseconds to microseconds), and/or phosphors, with a slow excited state decay time (typically microseconds to seconds).

Luminophores may be excited via a variety of processes, including by capturing radiation 30 and absorbing light. The luminophore may de-excite by emitting light (radiative) or by other mechanisms (non-radiative). The ratio of radiative events (emitted photons) to excitation events (e.g., absorbed photons) is called the quantum yield. Luminophores may have a quantum yield greater than 10%, 30%, 50%, 60%, 70%, 80%, or 90%. The light emitted from a luminophore (luminescence) has less energy (on average) than the energy of the excitation process, i.e., luminescence is not perfectly efficient. For photo-excited luminophores, the peak of the emission light is normally at a longer wavelength than the peak of the excitation spectrum. The difference is called the Stokes' shift. Generally, a larger Stokes' shift leads to less self-absorption of emission light and, hence, the emission light propagates further in solutions with larger Stokes' shifts. Luminophores may have a Stokes' shift of greater than 2 nm, 5 nm, 10 nm, 20 nm, 30 nm, or 50 nm.

In the process of scintillation, a material absorbs radiation, ionizing a molecule or atom and imparting energy into the material. The energy is transferred within the material until it excites a luminophore which then emits light of a characteristic spectrum. Scintillation materials 10 typically are combinations of several types of molecules, each efficient at a different part of the process. One component of scintillation materials 10, the scintillator 18, is efficient at capturing radiation. For example, the scintillator 18 may comprise (or may be) an organic molecule that includes an aromatic structure and/or an unsaturated carbon bond. As another example, the scintillator 18 may comprise (or may be) an atom that has a high cross section for neutron capture (e.g., lithium-6 ($^6$Li), boron-10 ($^{10}$B)). The scintillator 18 may be an efficient emitter of light (and hence may be a luminophore) and/or may be efficient at transmitting energy to other molecules.

Some scintillation materials 10 include a luminophore, e.g., primary luminophore 20, that may be excited by radiation 30 and/or the scintillator 18 and that efficiently emits light. This primary luminophore 20 may be excited by radiative and/or non-radiative energy transfer from the excited scintillator 18. Additionally or alternatively, scintillator 18 may include, or may be, a primary luminophore 20. Radiative energy transfer occurs when emission light from the scintillator 18 is absorbed by the primary luminophore 20. Non-radiative energy transfer occurs through various mechanisms such as molecular collisions (e.g., collisional quenching), exchange interactions, and excited state couplings (e.g., Förster energy transfer). Radiative and non-radiative energy transfer is enhanced by the overlap of the range of energy emitted upon de-excitation of the first molecule, the energy donor, and the range of energy required to excite the second molecule, the energy acceptor. For example, where the scintillator 18 is a luminophore, strong spectral overlap of its emission spectrum with the excitation spectrum of the primary luminophore 20 may lead to efficient energy transfer. Energy transfer also is strongly affected by the distance (and/or probability of proximity) between the energy donor and energy acceptor. Hence, condensed states (e.g., solids and liquids), high concentrations, and/or molecular associations may enhance energy transfer.

The emission spectrum of the scintillator 18 and/or the primary luminophore 20 may be dominated by deep UV (ultraviolet) light, which may not propagate far in certain materials and/or may be difficult to detect (e.g., with certain photodetectors 80). Thus, some scintillation materials 10 include a secondary luminophore 22, also known as a wavelength shifter and a wavelength converter, that may be excited by energy transfer from the scintillator 18 and/or primary luminophore 20 and that efficiently emits light of a longer wavelength than the emission from the scintillator 18 and/or primary luminophore 20. For example, the secondary luminophore 22 may have an excitation spectrum that overlaps with the emission spectrum of the scintillator 18 and/or the primary luminophore 20.

Scintillation materials 10 may include other components such as a host material 15 and/or solvent 16. The host material 15 and/or solvent 16 may contribute to the scintillation properties of the scintillation material 10 (e.g., by participating in radiation capture, energy transfer, and optical emission transmission) or may be essentially indifferent to the scintillation process. Host materials 15 and/or solvents 16 may provide other benefits to the scintillation material 10 and/or other components thereof, such as environmental protection, chemical stability, and/or mechanical stability.

The overall light yield of a scintillation material 10, the ratio of photons emitted to the energy of impinging radiation 30, is affected by the type, distribution, and/or amount of scintillator 18, optional primarily luminophore 20, optional secondary luminophore 22, and optional host material 15 and/or solvent 16. For example, as discussed herein, higher efficiency energy transfer may lead to a higher emission rate and thus a higher light yield. As another example, dilution, and consequent increase in average separation, of scintillator 18 in a solvent 16 may lead to a decrease in light yield. However, that decrease may not be linear if the solvent participates in the scintillation process (e.g., by transferring energy between the scintillator 18 and the primary luminophore 20).

Scintillation materials 10 may be solid (e.g., a crystal or polymeric plastic) and/or liquid. When a liquid, scintillation materials 10 may comprise a scintillant solution 14 that includes a solvent 16 and a scintillator 18, which, together form the bulk of the scintillant solution 14. The scintillation materials 10 and/or the scintillant solution 14 also may possess sufficient chemical energy to be used as a fuel. Hence, scintillation materials 10 may be fuel-scintillant compositions 12.

Fuel-scintillant compositions 12 scintillate when exposed to radiation 30 and possess sufficient chemical energy to be consumed to generate power (e.g., heat, electricity, work). For example, scintillant solutions 14, consisting at least of solvent 16 and scintillator 18, may be substantially composed of hydrocarbons, i.e., the scintillant solution 14, the solvent 16, and/or the scintillator 18 may include a principle component of hydrocarbons. Hydrocarbons may include hydrocarbon fuel, petroleum fuel, biofuel, unsaturated and/or saturated hydrocarbons (e.g., alkanes, alkenes, alkynes), linear hydrocarbons, branched hydrocarbons, cyclic hydrocarbons, aromatic hydrocarbons, and hydrocarbons substituted with one or more heteroatoms such as N, O, and S. Hydrocarbon fuels typically include linear alkanes with 6-16, 9-16, 6-12, 9-12, greater than 6, and/or greater than 8 carbon atoms. Hydrocarbon fuel may be fuel suited for combustion in an engine, e.g., an internal combustion engine. Fuel-scintillant compositions 12 may have a cetane number greater than 30, 40, 50, or 60, and may have an energy density (at 20° C.) of greater than 20 MJ/kg, 30 MJ/kg, or 40 MJ/kg. Illustrative, non-exclusive examples of hydrocarbon fuels include aviation fuel, jet fuel, kerosene, aviation gasoline, gasoline, and diesel fuel.

The solvent 16 of a fuel-scintillant composition 12 may appreciably transmit scintillation emission light 32, generated by radiation 30 absorbed within the fuel-scintillant composition 12. For example, the solvent 16 may be substantially transparent at one or more wavelengths of light (optionally all light) within the scintillation emission light 32 wavelength range. The solvent 16 may transmit greater than 90%/cm, 95%/cm, or 99%/cm of one or more wavelengths of light (optionally all light) within the scintillation emission light 32 wavelength range. Scintillation emission light 32 may be due to emission from the scintillator 18, the primary luminophore 20, and/or the secondary luminophore 22. Therefore scintillation emission light 32 may include light within the emission wavelength range of the scintillator 18, the primary luminophore 20, and/or the secondary luminophore 22. The scintillator emission light 32 wavelength range generally may be from 250-800 nm, or any range, or ranges, between, for example 250-450 nm, 250-350 nm, 300-350 nm, greater than 350 nm, greater than 380 nm, greater than 400 nm, and/or greater than 420 nm.

The solvent 16 generally includes a principle component of linear alkanes, e.g., linear alkanes with 6-16, 9-16, 6-12, 9-12, greater than 6, and/or greater than 8 carbon atoms. For example, the solvent 16 may be substantially or completely composed of octane, decane, dodecane, and mixtures thereof.

The scintillator 18 generally is soluble within the solvent 16 and may be present in the scintillant solution 14 at a weight percent of greater than 0.001%, 0.01%, 0.1%, 1%, 3%, 10%, 20%, or 30%, and/or less than 50%, 40%, 30%, 20%, 10%, 5%, 2%, or 1%.

The scintillator 18 generally includes a principle component of aromatic hydrocarbons, e.g., one or more fused, aromatic hydrocarbon rings each of 3-10, 3-8, 3-6, and/or 5-7 members, optionally substituted with one or more heteroatoms such as N, O, and/or S. For example, the scintillator may be substantially or completely composed of any combination of benzene, toluene, xylene, stilbene, terphenyl, polycyclic aromatic hydrocarbon, naphthalene, anthracene, and compounds including moieties thereof. Illustrative, non-exclusive examples of scintillators 18 include benzene, toluene, xylene, stilbene, p-terphenyl, 1,2,4-trimethylbenzene (TMB), ethyl benzene, alkyl benzene, phenyl xylyl ethane (PXE), and 2,5-diphenyloxazole (PPO).

The scintillant solution 14 may include a primary luminophore 20 (and/or the scintillator 18 may be a primary luminophore 20). The primary luminophore 20 generally is soluble within the solvent 16 and may be present in the scintillant solution 14 at a weight percent of greater than 0.0001%, 0.001%, 0.01%, 0.1%, 1%, 3%, 10%, 20%, or 30%, and/or less than 50%, 40%, 30%, 20%, 10%, 5%, 2%, or 1%. The primary luminophore 20 may be bound to, or otherwise molecularly associated with, the scintillator 18.

The primary luminophore 20 generally is an organic molecule, which may include an aromatic group (e.g., aromatic hydrocarbons), an aryl group, a phenyl group, an oxazole group, and/or an oxadiazole group. Illustrative, non-exclusive examples of primary luminophores 20 include terphenyl, p-terphenyl, polycyclic aromatic hydrocarbon, naphthalene, anthracene, PXE, PPO, DPA, 2-phenyl-5-(4-biphenylyl)-1,3,4-oxadiazole (PBD), 2-(4-tert-butylphenyl)-5-(4-phenylphenyl)-1,3,4-oxadiazole (b-PBD), and 9,10-diphenylanthracene (DPA).

The scintillant solution 14 may include a secondary luminophore 22. The secondary luminophore 22 generally is soluble within the solvent 16 and may be bound to, or otherwise molecularly associated with, the scintillator 18 and/or the primary luminophore 20. The secondary luminophore 22 may be present in the scintillant solution 14 at a weight percent of greater than 0.00001%, 0.0001%, 0.001%, 0.01%, 0.1%, or 1%, and/or less than 5%, 1%, 0.1%, 0.01%, or 0.001%.

The secondary luminophore 22 generally is an organic molecule, which may include an aromatic group (e.g., aromatic hydrocarbons), an aryl group, a phenyl group, a quaterphenyl group, an oxazole group, a pyrazole group, a pyrazoline group, a quinoline group, and/or a styryl group. Illustrative, non-exclusive examples of secondary luminophores 22 include p-bis-(o-methylstyryl)benzene (bis-MSB), PPO, 1,4-bis(5-phenyl-2-oxazolyl)benzene (POPOP), b-PBD, 1-phenyl-3-mesityl-2-pyrazoline (PMP), 1,3-diphenyl-2-pyrazoline, DPA, and p-quaterphenyl.

The scintillant solution 14 may include a neutron-sensitive adjunct 24, which has a high cross section for neutron capture. The neutron-sensitive adjunct 24 may be bound to, or otherwise molecularly associated with, the scintillator 18. The neutron-sensitive adjunct 24 may include atoms such as lithium-6 and/or boron-10 which have a high cross section for thermal neutron capture. Lithium-6 is one of the stable isotopes of lithium and has a natural abundance of about 7%. Hence, the neutron-sensitive adjunct 24 may comprise ions and/or compounds that incorporate natural lithium and/or lithium enriched in lithium-6. Boron-10 is one of the stable isotopes of boron and has a natural abundance of about 20%. Hence, the neutron-sensitive adjunct 24 may comprise ions and/or compounds that incorporate natural boron and/or boron enriched in boron-10. For example, the neutron-sensitive adjunct 24 may include borate, e.g., trimethyl borate.

The scintillant solution 14 may include a scintillation enhancer 26, which may be selected to enhance radiation 30 detection, discriminate radiation 30, inhibit chemical reactions (e.g., oxidation, corrosion), enhance chemical reactions (e.g., associations), stabilize the scintillant solution 14 (e.g., fuel stabilizer, metal chelator), inhibit growth (e.g., a biocide), improve lubrication, and/or improve viscosity (e.g., depress freezing point, reduce gelling). For example, the scintillation enhancer 26 may reduce the concentration of free oxygen within the scintillant solution 14. Free oxygen (e.g., molecular oxygen) present in the scintillant solution 14 may reduce scintillation light yield by quenching the excited state of the scintillator 18, the primary luminophore 20, and/or the secondary luminophore 22. The scintillation enhancer 26 may include an anti-oxidant, an oxygen scavenger, a reducing agent, a hygroscopic agent, a surfactant, a non-ionic surfactant (e.g., polyethylene glycol p-(1,1,3,3-tetramethylbutyl)-phenyl ether, sold under the trade name Triton-X-100), and/or a detergent.

Additionally or alternatively, free oxygen in the scintillant solution 14 and/or the fuel-scintillant composition 12 may be suppressed e.g., by the temporary presence of an oxygen scavenging agent and/or an oxygen displacing agent, and/or by oxygen removal processes. For example, oxygen may be displaced by subjecting the scintillant solution 14 and/or the fuel-scintillant composition 12 to bubbling with an inert gas, e.g., nitrogen and/or argon. As another example, oxygen may be removed by subjecting the scintillant solution 14 and/or the fuel-scintillant composition 12 to a vacuum. The result may be a fuel-scintillant composition 12 and/or a scintillant solution 14 that is essentially free of unbound oxygen. The concentration of unbound oxygen in the fuel-scintillant 12 and/or the scintillant solution 14 may be less than 100 ppm, 10 ppm, 1 ppm, 100 ppb, 10 ppb, and/or 1 ppb.

Figure 2:
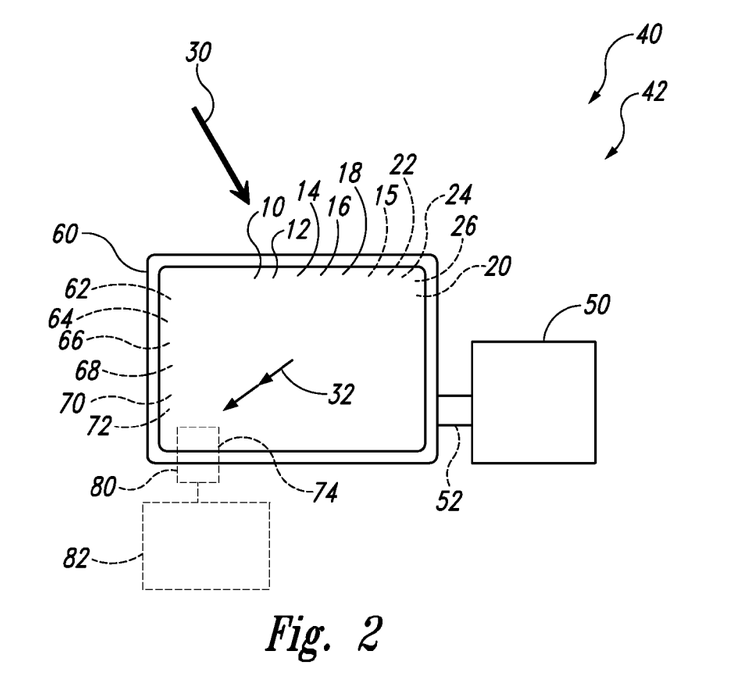
FIG. 2 is a schematic representation of radiation detection systems.

FIG. 2 is a schematic representation of radiation detection systems 40 which comprise, or are configured to use, fuel-scintillant compositions 12. Radiation detection systems 40 may be configured to detect, monitor, inspect, and/or verify the presence, amount, peak intensity, integrated intensity (dose), type, duration, decay rate, and/or time-structure of radiation 30 emanating from a location, a sample, and/or an object. Radiation detection systems 40 may be configured to detect ionic and/or neutral radiation, e.g., gamma radiation and/or neutrons, and may be configured to detect the flux (direction, amount, and/or duration) and/or type of radiation impinging on fuel-scintillant composition 12 contained in the fuel tank 60. Radiation detection systems 40 may be configured to discriminate the direction of radiation 30, for example discriminating radiation from space and radiation from terrestrial (non-space) sources (e.g., sources on and/or in the land, the sea, and/or the air). Radiation detection systems 40 may be configured to discriminate the duration of radiation 30 (e.g., the duration of a radiation emission event) and/or the total exposure (dose) of radiation 30, for example discriminating between short pulses and/or bursts of radiation 30 and continuous (or quasi-continuous) radiation 30.

Radiation detection systems 40 comprise a fuel tank 60 to contain a fuel-scintillant composition 12 and an engine 50 configured to consume fuel-scintillant composition 12 from the fuel tank 60. A radiation detection system 40 may be an installation, a structure, and/or a mobile apparatus (e.g., a radiation detection vehicle 42). Radiation detection systems 40 may include, or may be, radiation detection vehicles 42. Additionally or alternatively, radiation detection vehicles 42 may include a radiation detection system 40. In a radiation detection vehicle 42, the engine 50 is configured to propel, directly or indirectly, the vehicle by consuming the fuel-scintillant composition 12. Radiation detection vehicles 42 may be automated, manned, and/or unmanned. Illustrative, non-exclusive examples of radiation detection vehicles 42 include an aircraft (e.g., an airplane, a rotorcraft, a balloon, an unmanned aerial vehicle), a watercraft (e.g., a boat, a platform, a buoy), a land-craft (e.g., a car, a truck), and a spacecraft (e.g., a satellite).

Figure 3:
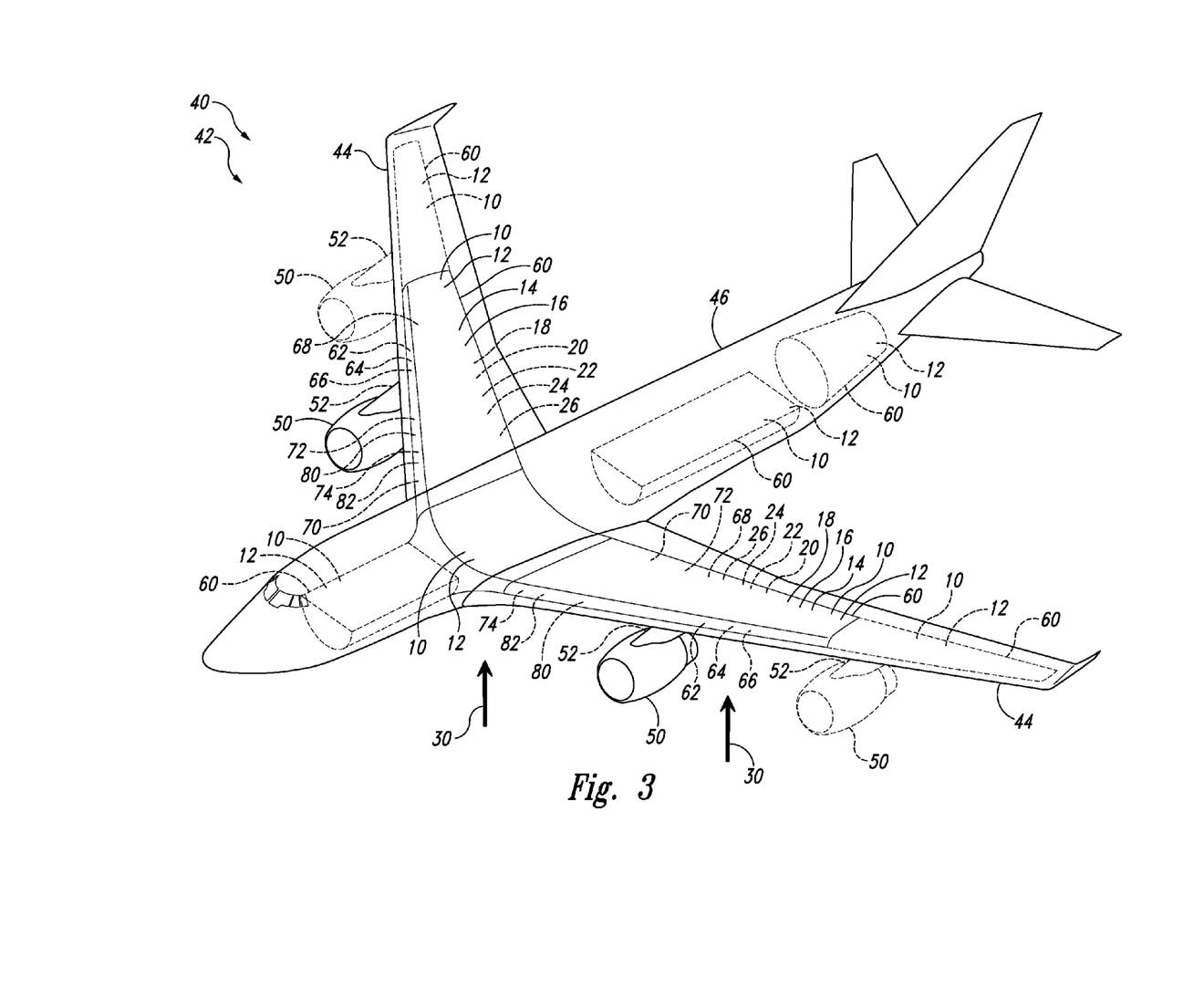
FIG. 3 is an illustrative, non-exclusive example of a radiation detection vehicle.

FIG. 3 shows an illustrative, non-exclusive example of a radiation detection vehicle 42 (an aircraft) with several optional configurations of engines 50 and fuel tanks 60. Fuel tanks 60 may be located on and/or in the radiation detection vehicle 42. Fuel tanks 60 may include flexible and/or rigid structure and may be at least partially defined by the superstructure, frame, and/or body of the radiation detection vehicle 42. For example, in FIG. 3, fuel tanks are shown in the wings 44 and/or the fuselage 46.

Engines 50 of a radiation detection system 40 may be configured to generate power by consuming the fuel-scintillant composition 12. For example, engine 50 may be an internal combustion engine, a jet engine, a ramjet, a gas turbine engine, and/or a diesel engine. Engines 50 may be configured to combust and/or decompose the fuel-scintillant 12. Engines 50 of a radiation detection vehicle 42 may be configured to provide power to batteries and/or electrical motors to propel the vehicle.

The radiation detection system 40 may be configured to transfer, automatically or under operator control, fuel-scintillant 12 in the fuel tank 60 to the engine 50 for consumption. For example, the radiation detection system 40 may include a fuel supply conduit 52.

Radiation detection systems 40 may be configured for high sensitivity detection, e.g., detection of weak and/or distant sources. For example, radiation detection systems 40 may be configured to detect gamma radiation sources of energy about 1 MeV per photon when the source is weaker than 100 MBq, 10 MBq, 1 MBq, 100 kBq, 10 kBq, or 1 kBq (one becquerel (Bq) equals one disintegration per second). Additionally or alternatively, radiation detection systems 40 may be configured to detect a radiation source further than 10 m, 30 m, 100 m, 200 m, 300 m, 500 m, 1,000 m, 2,000 m, or 3,000 m distant. High sensitivity detection may be aided by a large fuel-scintillant composition volume and/or cross sectional area. For example, fuel tanks 60 may be configured to define a large cross sectional area, generally perpendicular to the direction to the radiation source. Fuel tanks 60 may have a maximum cross sectional area greater than 5 $m^2$, 10 $m^2$, 20 $m^2$, 30 $m^2$, 40 $m^2$, 50 $m^2$, 60 $m^2$, 70 $m^2$, 80 $m^2$, 90 $m^2$, or 100 $m^2$. The maximum cross sectional area may be oriented generally horizontally, obliquely, or vertically to intersect the largest area of flux from the radiation source. In a radiation detection vehicle 42, the orientation may be determined and/or adjusted when the radiation detection vehicle is performing radiation detection. Additionally or alternatively, the orientation may be defined by the upright, operational position of the radiation detection vehicle 42.

Fuel tanks 60 may be configured to permit detection of scintillation emission light 32 from the fuel-scintillant composition 12 contained in the fuel tank 60. For example, a fuel tank 60 may include an optical interrogation port 74 and/or may at least partially accommodate (e.g., house, contain) a photodetector 80. An optical interrogation port 74 may be a window, fiber optic, optical system, and/or aperture in the fuel tank 60 that is at least partially transparent to scintillation emission light 32 emanating from the interior of the fuel tank 60. A photodetector 80 may be optically coupled to the fuel tank 60, the interior of the fuel tank 60, and/or the optical interrogation port 74.

Radiation detection systems 40 may include one or more photodetectors 80. The photodetectors 80 may be any suitable device configured to sense the scintillation emission light 32. Illustrative, non-exclusive examples of photodetectors 80 include a photomultiplier tube, phototube, a semiconductor photodetector, a photodiode, an avalanche photodiode, a phototransistor, a photoresistor, a photoconductor, a charge coupled device, an active pixel sensor, and a CMOS imager. The photodetector 80 may be sensitive to at least a portion of light within the range of 250-800 nm, or any range, or ranges, between, for example 250-450 nm, 250-350 nm, 300-350 nm, greater than 350 nm, greater than 380 nm, greater than 400 nm, and/or greater than 420 nm.

Radiation detection systems 40 may include a detection system 82 configured to determine the number, flux, type, peak intensity, integrated intensity (dose), decay rate, and/or time-structure of radiation events (e.g., scintillation emission events) within fuel-scintillant composition 12 contained in the fuel tank 60. The detection system 82 may be electrically coupled to the photodetector 80. The detection system 82 may include electronic test and measurement equipment, an analog to digital converter, a discriminator, a coincidence detector, a multi-channel analyzer, a pulse-shape analyzer, a computing device, a digital storage device, and/or a communication device.

Figure 4:
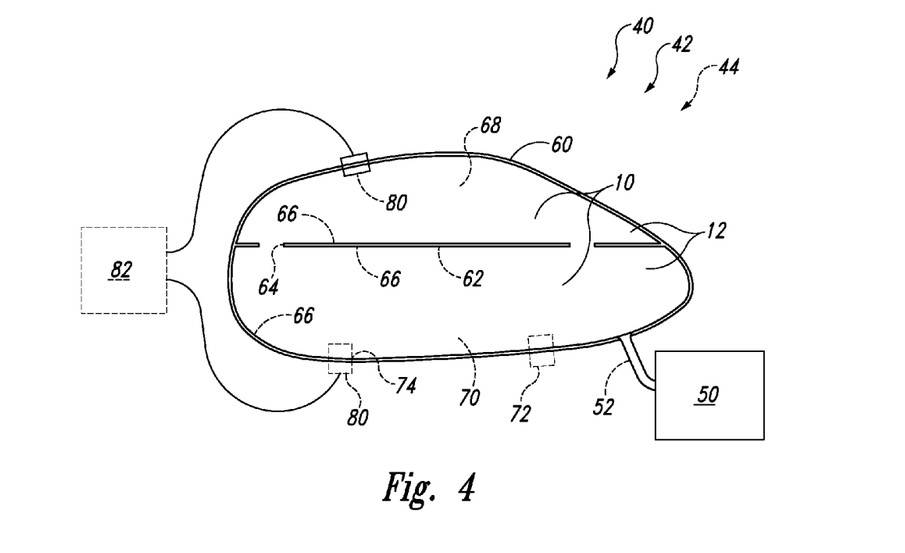
FIG. 4 is a cross section of an illustrative, non-exclusive example of a fuel tank configured for radiation monitoring.

Additionally or alternatively, fuel tanks 60 may include additional structure to aid detection and analysis of radiation 30. As illustrated in FIG. 4, fuel tank 60 may include a reflective structure 66 configured to reflect scintillation emission light 32, generally towards a photodetector 80. For example, the reflective structure 66 may be a reflective inner surface of the fuel tank 60. As another example, the reflective structure 66 may be a mirror, or mirror system, configured to concentrate light towards at least one of the photodetectors 80. Reflective structures 66 may have a reflectivity at one or more ranges within the wavelength range of the scintillation emission light 32 of greater than 50%, 80%, 90%, 95%, 98%, or 99%. Fuel tanks 60 may include an optical baffle 62 that at least partially optically isolates two regions within the fuel tank 60 (i.e., at least a first region 68 and a second region 70). The optical baffle 62 is configured to attenuate, optionally completely attenuate, light transfer between the first region 68 and the second region 70, e.g., light generated in the first region 68 does not penetrate into the second region 70. The optical baffle 62 may include one or more apertures 64 to allow the fuel-scintillant composition 12 to flow around and/or through the optical baffle 62. For example, the optical baffle 62 may be an opaque plate, fabric, foam, and/or mesh. Each region (e.g., the first region 68 and the second region 70) separated by the optical baffle 62 may be optically coupled to a different photodetector 80. Hence, scintillation emission light 32 from the first region 68 may be separately detected from scintillation emission light 32 from the second region 70. The separate regions may be configured to aid detection and/or discrimination of radiation 30 impinging on the fuel-scintillant composition 12 and the fuel tank 60. For example, an optical baffle 62 that separates an upper first region 68 from a lower second region 70 may enable discrimination of radiation emanating from above the fuel tank 60 (e.g., cosmic rays or other radiation 30 from space) and radiation emanating from below the fuel tank 60 (e.g., terrestrial (non-space) associated radiation 30).

Radiation detection systems 40 may include an additive injection system 72, which may be configured to supply to the fuel tank 60 a primary luminophore 20, a secondary luminophore 22, a neutron-sensitive adjunct 24, and/or a scintillation enhancer 26.

Figure 5:
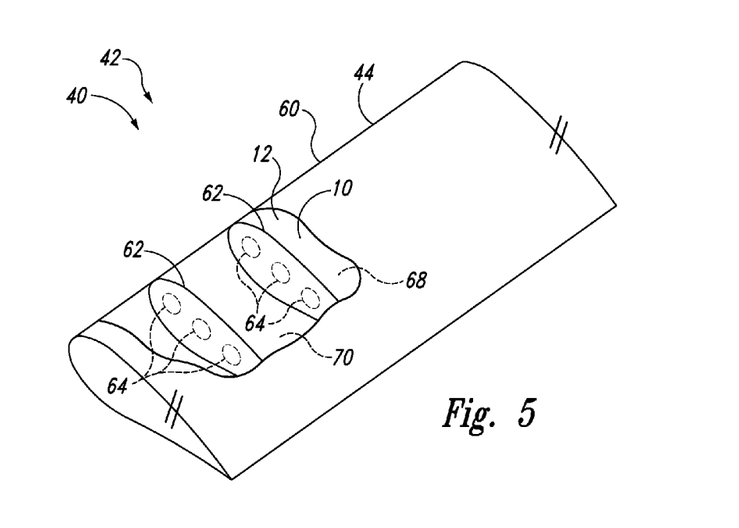
FIG. 5 is an illustrative, non-exclusive example of a fuel tank configured for radiation monitoring.

FIG. 5 shows an illustrative, non-exclusive example of a fuel tank 60 integrated within a radiation detection vehicle 42 (in a wing 44). The example of FIG. 5 is a fuel tank 60 similar in construction to the wet-wing design for aircraft. The fuel tank 60 is principally defined by the superstructure of the wing 44. Fuel-scintillant composition 12 is contained in the interior of the wing 44. The wing-integrated fuel tank 60 may include all of the optional elements discussed herein. For example, optical baffles 62 with apertures 64 are shown.

Figure 6:
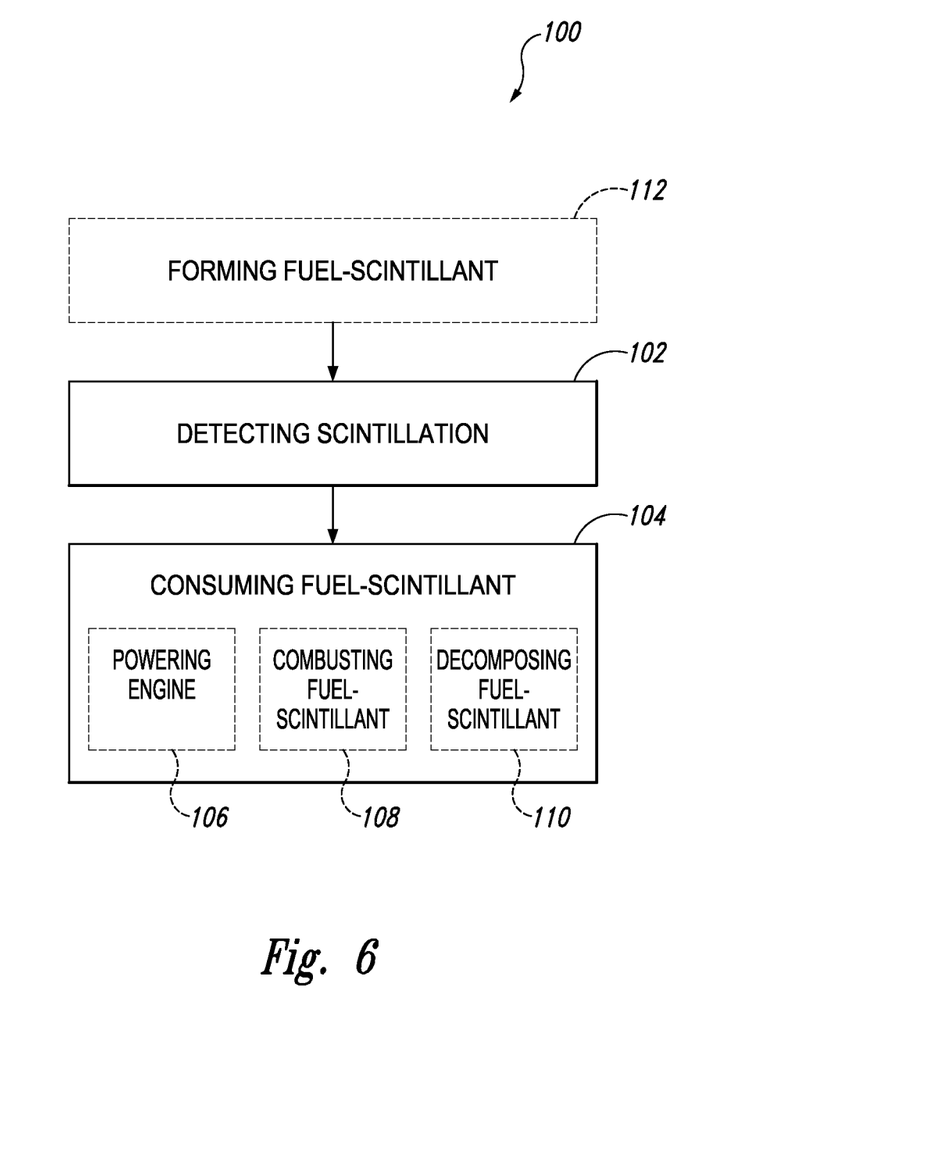
FIG. 6 is a schematic representation of methods of using fuel-scintillant compositions.

FIG. 6 schematically illustrates methods of detecting radiation 100 using the fuel-scintillant composition 12. Methods 100 comprise detecting 102 scintillation emission light 32 from the fuel-scintillant composition to detect radiation 30. Detecting 102 may include detecting radiation with the radiation detection system 40 and/or the radiation detection vehicle 42. Detecting 102 may include detecting at a distance from a radiation source, for example at a distance greater than 10 m, 30 m, 100 m, 200 m, 300 m, 500 m, 1,000 m, 2,000 m, or 3,000 m, and/or less than 3,000 m, 2,000 m, 1,000 m, 500 m, or 300 m. Further, detecting 102 may include aerially detecting a terrestrial radiation source. For example, methods 100 may be used to monitor a port of entry, national border, military zone, and/or combat zone for unauthorized radiation sources and/or nuclear materials. Because radiation detection systems 40 may be configured for detection of weak and/or distant sources, methods 100 may be used for remote and/or aerial monitoring. As examples, aircraft may monitor remote border regions; underground fuel tanks 60 may be used to monitor a remote land border; boats may monitor ports; and aircraft may search for undersea nuclear materials (e.g., associated with submarines).

Methods 100 also comprise consuming 104 the fuel-scintillant composition 12. Because the fuel-scintillant composition 12 has a high fuel value, methods 100 may use radiation detection systems 40 and/or radiation detection vehicles 42 to consume the fuel-scintillant composition 12, in which case the fuel-scintillant 12 may be used to fuel the engine 50 to generate power (i.e., powering 106 the engine 50). Additionally or alternatively, fuel-scintillant may be consumed to dispose of the fuel-scintillant composition 12 when no longer needed. For example, consuming 104 may include combusting 108 the fuel-scintillant composition 12 and/or decomposing 110 the fuel-scintillant composition 12.

Methods 100 may comprise forming 112 the fuel-scintillant composition 12 before the detecting 102. Forming 112 may include mixing a fuel with a scintillator 18, a primary luminophore 20, a secondary luminophore 22, a neutron-sensitive adjunct 24, and/or a scintillation enhancer 26. Forming 112 may be performed within the radiation detection system 40 and/or the radiation detection vehicle 42. For example, forming 112 may be performed as fuel is filling the fuel tank 60 and/or after the fuel is placed in the fuel tank 60 (e.g., by injecting a component of the fuel-scintillant composition 12 with the additive injection system 72).

An illustrative, non-exclusive example application of methods 100 is the use of a radiation detection vehicle 42 such as an airplane or an unmanned aerial vehicle to monitor a port of entry. The radiation detection vehicle 42 may be loaded (e.g., filled to capacity) with fuel-scintillant composition 12 and fly using the fuel-scintillant composition 12 as its fuel. The radiation detection vehicle 42 does not need to be configured to carry separate radiation detection media and fuel, thus, potentially extending the vehicle's flying time and/or sensitivity.

Another illustrative, non-exclusive example application of methods 100 is the use of a radiation detection vehicle 42 such as a satellite or an unmanned aerial vehicle to monitor pulsed radiation sources. The radiation detection vehicle 42 may be, or may include, a space telescope searching for gamma ray bursts from space, terrestrial gamma ray flashes associated with lightning, and/or pulsed radiation from weapons discharge.

Illustrative, non-exclusive examples of inventive subject matter according to the present disclosure are described in the following enumerated paragraphs:

A1. A fuel-scintillant composition comprising:
a scintillant solution including a hydrocarbon solvent and a scintillator;
wherein the scintillant solution is a hydrocarbon fuel for an engine.

A2. The fuel-scintillant composition of paragraph A1, wherein the scintillant solution and/or the hydrocarbon solvent is substantially at least one of aviation fuel, jet fuel, kerosene, aviation gasoline, gasoline, and diesel fuel.

A3. The fuel-scintillant composition of any of paragraphs A1-A2, wherein the hydrocarbon solvent includes a principle component of unsaturated and/or saturated hydrocarbons, optionally alkanes including 6-16, 9-16, 6-12, 9-12, greater than 6, and/or greater than 8 carbon atoms.

A4. The fuel-scintillant composition of any of paragraphs A1-A3, wherein the hydrocarbon solvent is substantially transparent across a scintillator emission wavelength range.

A4.1. The fuel-scintillant composition of paragraph A4, wherein the scintillator emission wavelength range is from 250-800 nm, 250-450 nm, 250-350 nm, and/or 300-350 nm.

A4.2. The fuel-scintillant composition of any of paragraphs A4-A4.1, wherein the hydrocarbon solvent transmits greater than 90%/cm, 95%/cm, or 99%/cm of light across the scintillator emission wavelength range.

A5. The fuel-scintillant composition of any of paragraphs A1-A4.2, wherein the scintillator is a primary luminophore, optionally wherein the primary luminophore is a fluorophore and/or a phosphor.

A6. The fuel-scintillant composition of any of paragraphs A1-A5, wherein the weight percent of the scintillator in the scintillant solution is greater than 0.001%, 0.01%, 0.1%, 1%, 3%, 10%, 20%, or 30%, and/or less than 50%, 40%, 30%, 20%, 10%, 5%, 2%, or 1%.

A7. The fuel-scintillant composition of any of paragraphs A1-A6, wherein the scintillator includes an aromatic hydrocarbon, optionally a benzene moiety.

A8. The fuel-scintillant composition of any of paragraphs A1-A7, wherein the scintillator includes one or more compounds selected from the group consisting of benzene, toluene, xylene, stilbene, terphenyl, p-terphenyl, polycyclic aromatic hydrocarbon, naphthalene, anthracene, TMB, ethyl benzene, alkyl benzene, PXE, and PPO.

A9. The fuel-scintillant composition of any of paragraphs A1-A8, wherein the scintillant solution further includes a primary luminophore.

A9.1. The fuel-scintillant composition of paragraph A9, wherein the primary luminophore is a fluorophore and/or a phosphor.

A9.2. The fuel-scintillant composition of any of paragraphs A9-A9.1, wherein the weight percent of the primary luminophore in the scintillant solution is greater than 0.0001%, 0.001%, 0.01%, 0.1%, 1%, 3%, 10%, 20%, or 30%, and/or less than 50%, 40%, 30%, 20%, 10%, 5%, 2%, or 1%.

A9.3. The fuel-scintillant composition of any of paragraphs A9-A9.2, wherein the primary luminophore includes an aromatic group, an aryl group, a phenyl group, an oxazole group, and/or an oxadiazole group.

A9.4. The fuel-scintillant composition of any of paragraphs A9-A9.3, wherein the primary luminophore includes one or more compounds selected from the group consisting of terphenyl, p-terphenyl, polycyclic aromatic hydrocarbon, naphthalene, anthracene, PXE, PPO, PBD, b-PBD, and DPA.

A10. The fuel-scintillant composition of any of paragraphs A1-A9.4, wherein the scintillant solution further includes a secondary luminophore.

A10.1. The fuel-scintillant composition of paragraph A10, wherein the secondary luminophore is a fluorophore and/or a phosphor.

A10.2. The fuel-scintillant composition of any of paragraphs A10-A10.1, wherein the secondary luminophore has an excitation spectrum that overlaps with an emission spectrum of the scintillator and/or, when present, a primary luminophore.

A10.3. The fuel-scintillant composition of any of paragraphs A10-A10.2, wherein the secondary luminophore has a luminescence emission at greater than 350 nm, 380 nm, 400 nm, and/or 420 nm.

A10.4. The fuel-scintillant composition of any of paragraphs A10-A10.3, wherein the weight percent of the secondary luminophore in the scintillant solution is greater than 0.00001%, 0.0001%, 0.001%, 0.01%, 0.1%, or 1%, and/or less than 5%, 1%, 0.1%, 0.01%, or 0.001%.

A10.5. The fuel-scintillant composition of any of paragraphs A10-A10.4, wherein the secondary luminophore includes an aromatic group, an aryl group, a phenyl group, a quaterphenyl group, an oxazole group, a pyrazole group, a pyrazoline group, a quinoline group, and/or a styryl group.

A10.6. The fuel-scintillant composition of any of paragraphs A10-A10.5, wherein the secondary luminophore includes one or more compounds selected from the group consisting of bis-MSB, PPO, POPOP, b-PBD, PMP, 1,3-diphenyl-2-pyrazoline, DPA, and p-quaterphenyl.

A11. The fuel-scintillant composition of any of paragraphs A1-A10.6, wherein the scintillant solution further includes a neutron-sensitive adjunct, optionally wherein the neutron-sensitive adjunct includes lithium, lithium-6, boron, boron-10, and/or borate.

A12. The fuel-scintillant composition of any of paragraphs A1-A11, further comprising: a scintillation enhancer.

A12.1. The fuel-scintillant composition of paragraph A12, wherein the scintillation enhancer is one or more of an anti-oxidant, an oxygen scavenger, a reducing agent, and a hygroscopic agent.

A12.2. The fuel-scintillant composition of any of paragraphs A12-A12.1, wherein the scintillation enhancer includes one or more compounds selected from the group of a surfactant, a non-ionic surfactant, and polyethylene glycol p-(1,1,3,3-tetramethylbutyl)-phenyl ether.

A13. The fuel-scintillant composition of any of paragraphs A1-A12.2, wherein the fuel-scintillant composition has an unbound oxygen concentration of less than 100 ppm, 10 ppm, 1 ppm, 100 ppb, 10 ppb, and/or 1 ppb.

B1. A radiation detection vehicle comprising:
  a fuel tank containing a fuel-scintillant composition; and
  an engine configured to propel the vehicle by consuming the fuel-scintillant composition;
  wherein the vehicle is configured to detect radiation with the fuel-scintillant composition.

B2. The radiation detection vehicle of paragraph B1, wherein the vehicle is at least one of an aircraft, a watercraft, a land-craft, a spacecraft, an unmanned vehicle, an automated vehicle, and an unmanned aerial vehicle.

B3. The radiation detection vehicle of any of paragraphs B1-B2, wherein the fuel-scintillant composition is the fuel-scintillant composition of any of paragraphs A1-A13.

B4. The radiation detection vehicle of any of paragraphs B1-B3, wherein the vehicle is configured to detect at least one of gamma radiation and neutrons.

B5. The radiation detection vehicle of any of paragraphs B1-B4, wherein the vehicle is configured to detect at least one of the amount, flux, type, peak intensity, integrated intensity, dose, decay rate, and/or time-structure of radiation impinging on fuel-scintillant composition contained in the fuel tank.

B6. The radiation detection vehicle of any of paragraphs B1-B5, wherein the vehicle is configured to discriminate the direction of radiation, optionally wherein the vehicle is configured to discriminate radiation from space and radiation from terrestrial sources.

B7. The radiation detection vehicle of any of paragraphs B1-B6, wherein the vehicle is configured to discriminate a duration of radiation, a duration of a radiation emission event, and/or a total exposure of radiation, optionally wherein the vehicle is configured to discriminate between short pulses and/or bursts of radiation and continuous and/or quasi-continuous radiation.

B8. The radiation detection vehicle of any of paragraphs B1-B7, wherein the engine is configured to generate power by combusting the fuel-scintillant composition.

B9. The radiation detection vehicle of any of paragraphs B1-B8, wherein the engine includes, and optionally is, at least one of an internal combustion engine, a jet engine, a ramjet, a gas turbine engine, and a diesel engine.

B10. The radiation detection vehicle of any of paragraphs B1-B9, wherein the engine supplies power to at least one of a battery and an electric motor that directly or indirectly propels the radiation detection vehicle.

B11. The radiation detection vehicle of any of paragraphs B1-B10, further comprising a fuel supply conduit configured to transfer fuel-scintillant from the fuel tank to the engine.

B12. The radiation detection vehicle of any of paragraphs B1-B11, wherein the fuel tank is at least partially within a wing and/or a fuselage of the vehicle.

B13. The radiation detection vehicle of any of paragraphs B1-B12, wherein the fuel tank has a maximum cross sectional area greater than 5 $m^2$, 10 $m^2$, 20 $m^2$, 30 $m^2$, 40 $m^2$, 50 $m^2$, 60 $m^2$, 70 $m^2$, 80 $m^2$, 90 $m^2$, or 100 $m^2$, optionally wherein the maximum cross sectional area is in a horizontal plane when the vehicle is in an upright operational position.

B14. The radiation detection vehicle of any of paragraphs B1-B13, wherein the fuel tank is configured to permit detection of scintillation emission light from the fuel-scintillant composition, optionally wherein the fuel tank includes at least one optical interrogation port.

B15. The radiation detection vehicle of any of paragraphs B1-B14, further comprising at least one photodetector configured to detect scintillation emission light from the fuel-scintillant composition contained in the fuel tank.

B15.1. The radiation detection vehicle of paragraph B15, wherein the photodetector is optically coupled to an interior of the fuel tank.

B15.2. The radiation detection vehicle of any of paragraphs B15-B15.1, wherein the photodetector includes a photomultiplier tube and/or a semiconductor photodetector.

B15.3. The radiation detection vehicle of any of paragraphs B15-B15.2, wherein the photodetector is sensitive to scintillation emission light from the fuel-scintillant composition, optionally within the range of 250-800 nm, 250-450 nm, 250-350 nm, and/or 300-350 nm.

B15.4. The radiation detection vehicle of any of paragraphs B15-B15.3, further comprising a detection system configured to determine at least one of the number, flux, type, peak intensity, integrated intensity, dose, and/or time-structure of radiation events within fuel-scintillant composition contained in the fuel tank by measuring the output of the photodetector.

B15.4.1. The radiation detection vehicle of paragraph B15.4, wherein the detection system includes one or more of a discriminator, a coincidence detector, a multi-channel analyzer, and a pulse-shape analyzer.

B16. The radiation detection vehicle of any of paragraphs B1-B15.4.1, wherein the fuel tank includes a reflective structure, optionally configured to reflect light towards a photodetector optically coupled to the fuel tank.

B17. The radiation detection vehicle of any of paragraphs B1-B16, wherein the fuel tank includes an optical baffle, optionally wherein the optical baffle is configured to at least partially optically isolate two regions within the fuel tank.

B17.1. The radiation detection vehicle of paragraph B17, wherein each of the two regions is optically coupled to a different photodetector.

B17.2. The radiation detection vehicle of any of paragraphs B17-B17.1, wherein the optical baffle separates an upper region from a lower region.

B18. The radiation detection vehicle of any of paragraphs B1-B17.2, further comprising an additive injection system, optionally wherein the additive injection system is configured to supply to the fuel tank one or more of a primary luminophore, a secondary luminophore, a neutron-sensitive adjunct, and a scintillation enhancer.

C1. A method of radiation detection comprising:
  detecting scintillation emission light from a fuel-scintillant composition to detect radiation; and
  consuming the fuel-scintillant composition.

C2. The method of paragraph C1, wherein the fuel-scintillant composition is the fuel-scintillant composition of any of paragraphs A1-A13.

C3. The method of any of paragraphs 01-02, further comprising selecting the fuel-scintillant composition of any of paragraphs A1-A13.

C4. The method of any of paragraphs C1-03, wherein the detecting includes detecting with the radiation detection vehicle of any of paragraphs B1-B18 and wherein the consuming includes consuming the fuel-scintillant to power the radiation detection vehicle.

C5. The method of any of paragraphs 01-04, wherein the detecting includes detecting at a distance from a radiation source, optionally wherein the distance is greater than 10 m, 30 m, 100 m, 200 m, 300 m, 500 m, 1,000 m, 2,000 m, or 3,000 m, and/or less than 3,000 m, 2,000 m, 1,000 m, 500 m, or 300 m.

C6. The method of any of paragraphs 01-05, wherein the detecting includes aerially detecting a terrestrial radiation source.

C7. The method of any of paragraphs 01-06, wherein the detecting includes detecting near a port of entry.

C8. The method of any of paragraphs C1-07, wherein the detecting includes detecting at least one of gamma radiation and neutrons.

C9. The method of any of paragraphs C1-08, wherein the detecting includes detecting at least one of the amount, flux, type, peak intensity, integrated intensity, dose, decay rate, and/or time-structure of radiation.

C10. The method of any of paragraphs 01-09, wherein the detecting includes discriminating the direction of radiation and optionally discriminating radiation from space and radiation from terrestrial sources.

C11. The method of any of paragraphs C1-010, wherein the detecting includes discriminating a duration of radiation, a duration of a radiation emission event, and/or a total exposure of radiation, and optionally wherein the detecting includes discriminating between short pulses and/or bursts of radiation and continuous and/or quasi-continuous radiation.

C12. The method of any of paragraphs C1-C11, wherein the detecting includes determining at least one of the number, flux, type, peak intensity, integrated intensity, dose, and/or time-structure of radiation events within the fuel-scintillant composition.

C13. The method of any of paragraphs C1-012, wherein the consuming includes powering an engine, optionally in at least one of an internal combustion engine, a jet engine, a ramjet, a gas turbine engine, and a diesel engine.

C14. The method of any of paragraphs 01-013, wherein the consuming includes combusting the fuel-scintillant composition.

C15. The method of any of paragraphs C1-C14, wherein the consuming includes decomposing the fuel-scintillant composition.

C16. The method of any of paragraphs C1-015, further comprising forming the fuel-scintillant composition by mixing, before the detecting, a fuel with one or more of a scintillator, a primary luminophore, a secondary luminophore, a neutron-sensitive adjunct, and a scintillation enhancer.

C16.1. The method of paragraph C16, wherein the fuel is substantially at least one of aviation fuel, jet fuel, kerosene, aviation gasoline, gasoline, and diesel fuel.

C16.2. The method of any of paragraphs C16-016.1, further comprising selecting the fuel, wherein the fuel is substantially at least one of aviation fuel, jet fuel, kerosene, aviation gasoline, gasoline, and diesel fuel.

C16.3. The method of any of paragraphs 016-016.2, wherein the forming is performed within a radiation detection system, optionally within a radiation detection vehicle of any of paragraphs B1-B18.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required of all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A radiation detection vehicle comprising:
   a fuel tank containing a fuel-scintillant composition; and
   an engine configured to propel the vehicle by consuming the fuel-scintillant composition;
   wherein the vehicle is configured to detect radiation with the fuel-scintillant composition.

2. The radiation detection vehicle of claim 1, wherein the vehicle is an aircraft.

3. The radiation detection vehicle of claim 2, wherein the fuel tank is at least partially within a wing of the aircraft.

4. The radiation detection vehicle of claim 1, wherein the engine is at least one of an internal combustion engine, a jet engine, a ramjet, a gas turbine engine, and a diesel engine.

5. The radiation detection vehicle of claim 1, wherein the fuel tank has a maximum cross sectional area greater than 20 $m^2$.

6. The radiation detection vehicle of claim 1, further comprising at least one photodetector configured to detect scintillation emission light from the fuel-scintillant composition contained in the fuel tank.

7. The radiation detection vehicle of claim 6, further comprising a detection system configured to determine at least one of a number, flux, type, peak intensity, integrated intensity, and time-structure of radiation events within the fuel-scintillant composition contained in the fuel tank by measuring an output of the photodetector.

8. The radiation detection vehicle of claim 1, wherein the fuel tank includes a reflective structure configured to reflect light towards a photodetector optically coupled to the fuel tank.

9. The radiation detection vehicle of claim 1, wherein the fuel tank includes an optical baffle that is configured to at least partially optically isolate two regions within the fuel tank.

10. The radiation detection vehicle of claim 9, wherein each of the two regions is optically coupled to a different photodetector.

11. The radiation detection vehicle of claim 9, wherein the optical baffle separates an upper region from a lower region.

12. The radiation detection vehicle of claim 9, further comprising an additive injection system configured to supply to the fuel tank one or more of a primary luminophore, a secondary luminophore, a neutron-sensitive adjunct, and a scintillation enhancer.

13. A method of radiation detection with a radiation detection vehicle that includes a fuel tank and an engine, the method comprising:
    detecting scintillation emission light from a fuel-scintillant composition in the fuel tank to detect radiation; and
    combusting the fuel-scintillant composition with the engine to power the radiation detection vehicle.

14. The method of claim 13, wherein the fuel-scintillant composition is substantially at least one of aviation fuel, jet fuel, kerosene, aviation gasoline, gasoline, and diesel fuel.

15. The method of claim 13, further comprising forming the fuel-scintillant composition by mixing, before the detecting, a fuel with one or more of a scintillator, a primary luminophore, a secondary luminophore, a neutron-sensitive adjunct, and a scintillation enhancer.

16. The method of claim 13, wherein the radiation detection vehicle is an aircraft and the detecting includes aerially detecting a terrestrial radiation source.

17. The method of claim 13, wherein the detecting includes detecting at a distance from a radiation source and wherein the distance is greater than 300 m.

18. The method of claim 13, wherein the detecting includes detecting at least one of gamma radiation and neutrons.

19. The method of claim 13, wherein the detecting includes discriminating radiation from space and radiation from terrestrial sources.

20. The method of claim 13, wherein the detecting includes determining at least one of a number, flux, type, peak intensity, integrated intensity, dose, and/or time-structure of radiation events within the fuel-scintillant composition.

* * * * *